(12) United States Patent
Ho et al.

(10) Patent No.: US 9,188,547 B2
(45) Date of Patent: Nov. 17, 2015

(54) DEFECT INSPECTION APPARATUS AND METHOD

(71) Applicant: TAIWAN SEMICONDUCTOR MANUFACTURING CO., LTD., Hsinchu (TW)

(72) Inventors: Chun-Yen Ho, Changhua County (TW); Tsung-Hsien Lee, Tainan (TW); Han-Tang Lo, Hsinchu (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 56 days.

(21) Appl. No.: 14/062,802

(22) Filed: Oct. 24, 2013

(65) Prior Publication Data

US 2015/0116701 A1 Apr. 30, 2015

(51) Int. Cl.
*G01N 21/88* (2006.01)
*G01N 21/95* (2006.01)
*H01L 21/66* (2006.01)

(52) U.S. Cl.
CPC ............ *G01N 21/9501* (2013.01); *H01L 22/20* (2013.01)

(58) Field of Classification Search
CPC ............ G01N 21/956; G01N 21/9501; G01N 21/95607; G06T 7/0004; G06T 7/0002; H01L 22/12; H01L 21/67288
USPC ............... 356/237.1–237.5; 438/16, 107, 113
See application file for complete search history.

(56) References Cited

U.S. PATENT DOCUMENTS

| | | | |
|---|---|---|---|
| 5,943,551 A * | 8/1999 | Schemmel et al. | 438/14 |
| 6,156,625 A * | 12/2000 | Balamurugan | 438/462 |
| 6,812,550 B1 * | 11/2004 | En et al. | 257/629 |
| 2005/0152594 A1 * | 7/2005 | Jau et al. | 382/145 |
| 2007/0035728 A1 * | 2/2007 | Kekare et al. | 356/237.5 |
| 2008/0188016 A1 * | 8/2008 | Pare et al. | 438/16 |
| 2014/0192352 A1 * | 7/2014 | Bamba et al. | 356/237.5 |

\* cited by examiner

*Primary Examiner* — Hoa Pham
(74) *Attorney, Agent, or Firm* — McDermott Will & Emery LLP (57) ABSTRACT

A defect inspection apparatus is disclosed that includes a stage, a photosensitive element, and a controller. The stage can support a semiconductor element that has a plurality of complete dies and partial dies surrounding the complete dies. The photosensitive element is located above the stage. The controller is electrically connected to the photosensitive element to drive the photosensitive element to inspect the defects of the complete dies and the partial dies.

20 Claims, 9 Drawing Sheets

DEFECT INSPECTION APPARATUS AND METHOD

FIELD

The present disclosure relates to a defect inspection apparatus and a defect inspection method.

BACKGROUND

With the development of science and technology, there are a wide variety of electric products provided in the consumer market. Therefore, different sizes of semiconductor elements are required for the electrical products.

When a wafer includes large dies or slender dies, there are partial dies (i.e., incomplete dies) surrounding complete dies formed at the edge of the wafer. However, since conventional defect scan tools can only focus on the complete dies of the wafer, additional devices, such as optical microscope (OM) and scanning electron microscope (SEM), are required to check if defects exist in the partial dies.

As result, if the wafers suffer from vibrations in the process, the conventional defect scan tools only can inspect the defect and collect defect information of the complete dies without the defect information of the partial dies at the same time. Technicians need to spend much more time confirming that the partial die area is defect free through the additional devices.

BRIEF DESCRIPTION OF THE DRAWINGS

The disclosure can be more fully understood by reading the following detailed description of various embodiments, with reference to the accompanying drawings as follows.

DETAILED DESCRIPTION

In the following description, specific details are presented to provide a thorough understanding of the embodiments of the present disclosure. Persons of ordinary skill in the art will recognize, however, that the present disclosure can be practiced without one or more of the specific details, or in combination with other components. Well-known implementations or operations are not shown or described in detail to avoid obscuring aspects of various embodiments of the present disclosure.

The terms used in this specification generally have their ordinary meanings in the art and in the specific context where each term is used. The use of examples in this specification, including examples of any terms discussed herein, is illustrative only, and in no way limits the scope and meaning of the disclosure or of any exemplified term. Likewise, the present disclosure is not limited to various embodiments given in this specification.

It will be understood that, although the terms "first," "second," etc., may be used herein to describe various elements, these elements should not be limited by these terms. These terms are used to distinguish one element from another. For example, a first element could be termed a second element, and, similarly, a second element could be termed a first element, without departing from the scope of the embodiments. As used herein, the term "and/or" includes any and all combinations of one or more of the associated listed items.

As used herein, the terms "comprising," "including," "having," "containing," "involving," and the like are to be understood to be open-ended, i.e., to mean including but not limited to.

Reference throughout the specification to "one embodiment" or "an embodiment" means that a particular feature, structure, implementation, or characteristic described in connection with the embodiment is included in at least one embodiment of the present disclosure. Thus, uses of the phrases "in one embodiment" or "in an embodiment" in various places throughout the specification are not necessarily all referring to the same embodiment. Furthermore, the particular features, structures, implementation, or characteristics may be combined in any suitable manner in one or more embodiments.

Figure 1:
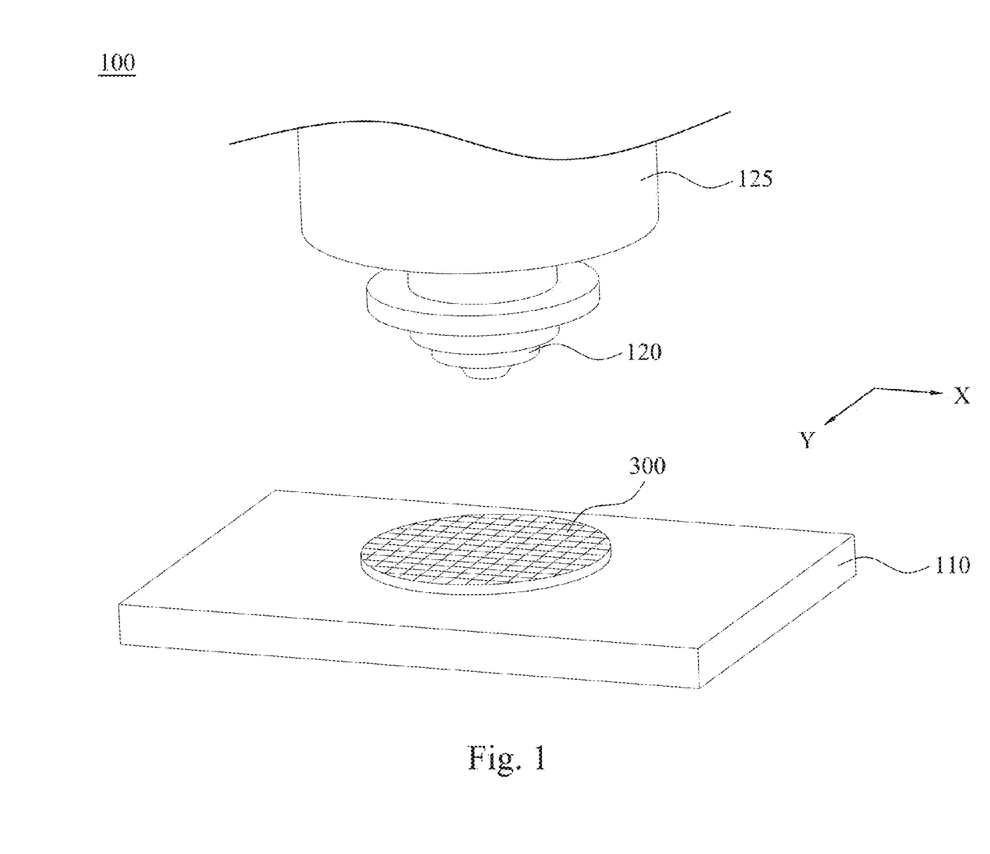
FIG. 1 is a perspective view of a defect inspection apparatus in accordance with some embodiments of the present disclosure.
Figure 2:
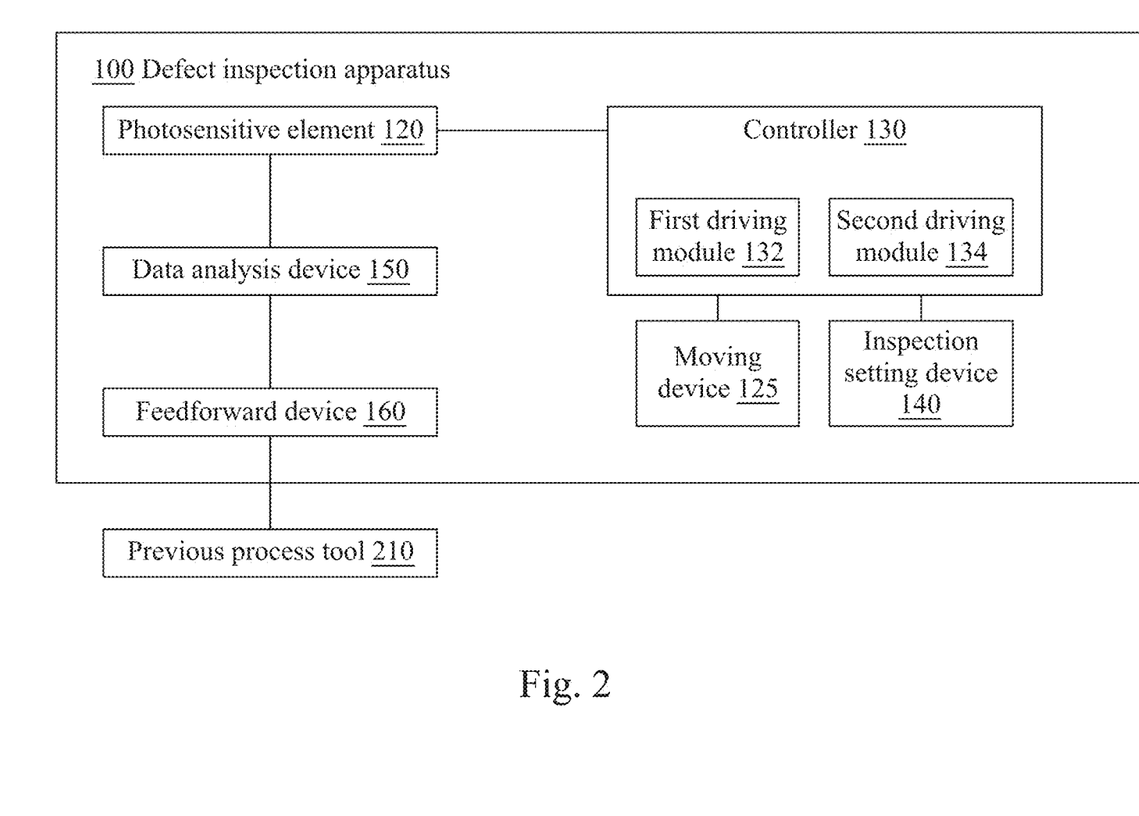
FIG. 2 is a block diagram of the defect inspection apparatus connected to a previous process tool shown in FIG. 1.

FIG. 1 illustrates a perspective view of a defect inspection apparatus 100 in accordance with some embodiments of the present disclosure. FIG. 2 illustrates a block diagram of the defect inspection apparatus 100 connected to a previous process tool 210 illustrated in FIG. 1. As illustrated in FIG. 1 and FIG. 2, the defect inspection apparatus 100 includes a stage 110, a photosensitive element 120, and a controller 130. The stage 110 can support a semiconductor element 300, such as a wafer, but not limited in the present disclosure.

The photosensitive element 120 is located above the stage 110, and may include a charge coupled device (CCD) camera. The controller 130 is electrically connected to the photosensitive element 120. In operation, the controller 130 drives the photosensitive element 120 to inspect the defects of the semiconductor element 300.

Figure 3:
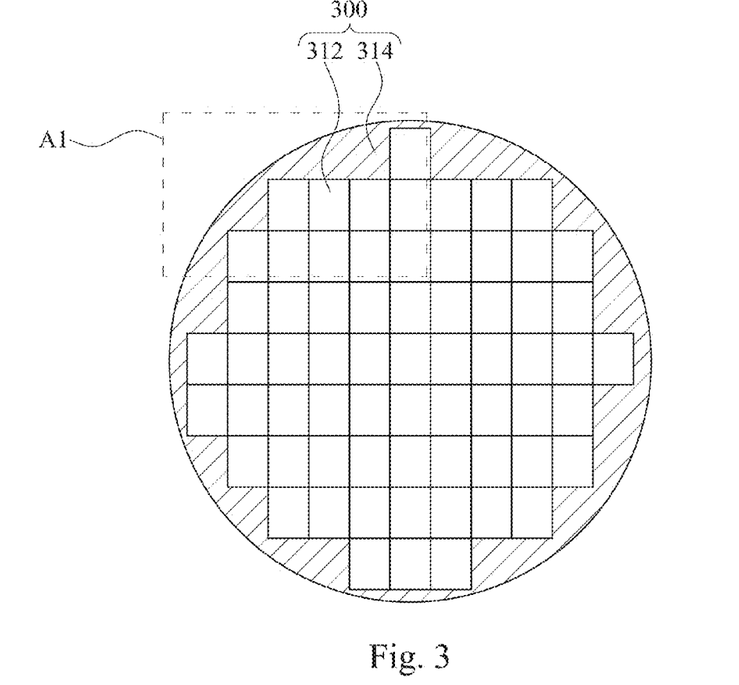
FIG. 3 is a top view of the semiconductor element when being inspected by a photosensitive element shown in FIG. 1.

FIG. 3 is a top view of the semiconductor element 300 when being inspected by the photosensitive element 120 shown in FIG. 1. As shown in FIG. 2 and FIG. 3, the semiconductor element 300 has a plurality of complete dies 312 and partial dies 314 (i.e., incomplete dies), and the complete dies 312 are large dies. The partial dies 314 are at the edge portion of the semiconductor element 300 and thus surround the complete dies 312. The controller 130 can drive the photosensitive element 120 to inspect the defects of the complete dies 312 and the defects of the partial dies 314.

In some embodiments, the controller 130 includes a first driving module 132 and a second driving module 134. The first and second driving modules 132, 134 are electrically connected to the photosensitive element 120. In operation, the first driving module 132 drives the photosensitive element 120 to inspect the defects of the complete dies 312. Moreover, the second driving module 134 drives the photosensitive element 120 to inspect the defects of the partial dies 314.

When the photosensitive element 120 inspects the semiconductor element 300, the photosensitive element 120 may position an inspection area A1 on a portion of the complete dies 312 and a portion of the partial dies 314. In some embodiments, the defect inspection apparatus 100 further includes a moving device 125 (see FIG. 1 and FIG. 2). The moving device 125 is connected to the photosensitive element 120 and electrically connected to the controller 130. In operation, the controller 130 can drive the moving device 125 to move the photosensitive element 120 over the semiconductor element 300 in directions X, Y.

Moreover, the defect inspection apparatus 100 may further include an inspection setting device 140. The inspection setting device 140 is electrically connected to the first and second driving modules 132, 134 of the controller 130. Users can choose a function on the inspection setting device 140 to inspect the defects of the complete dies 312, the defects of the partial dies 314, or the combinations thereof, such that an inspection signal may be sent to the photosensitive element 120.

Figure 4:
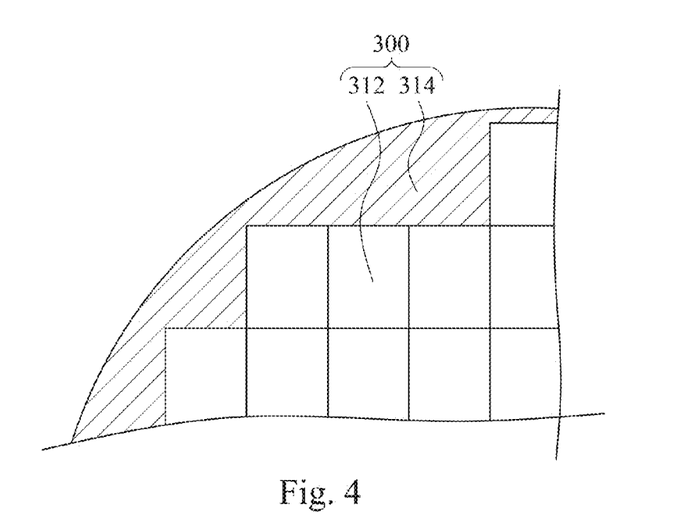
FIG. 4 is a partial enlarged view of the semiconductor element within an inspection area of the photosensitive element shown in FIG. 3.

FIG. 4 is a partial enlarged view of the semiconductor element 300 within the inspection area A1 of the photosensitive element 120 shown in FIG. 3. The inspection area A1 may be smaller than the semiconductor element 300, but the present disclosure is not limited in this regard. However, referring to FIG. 1 and FIG. 3, the inspection area A1 on the semiconductor element 300 can move along with the photosensitive element 120, such that the defects of the complete dies 312 and the defects of the partial dies 314 can be scanned by the inspection area A1 of the photosensitive element 300.

It is to be noted that the connection relationships of the elements described above will not be repeated in the following description.

Figure 5:
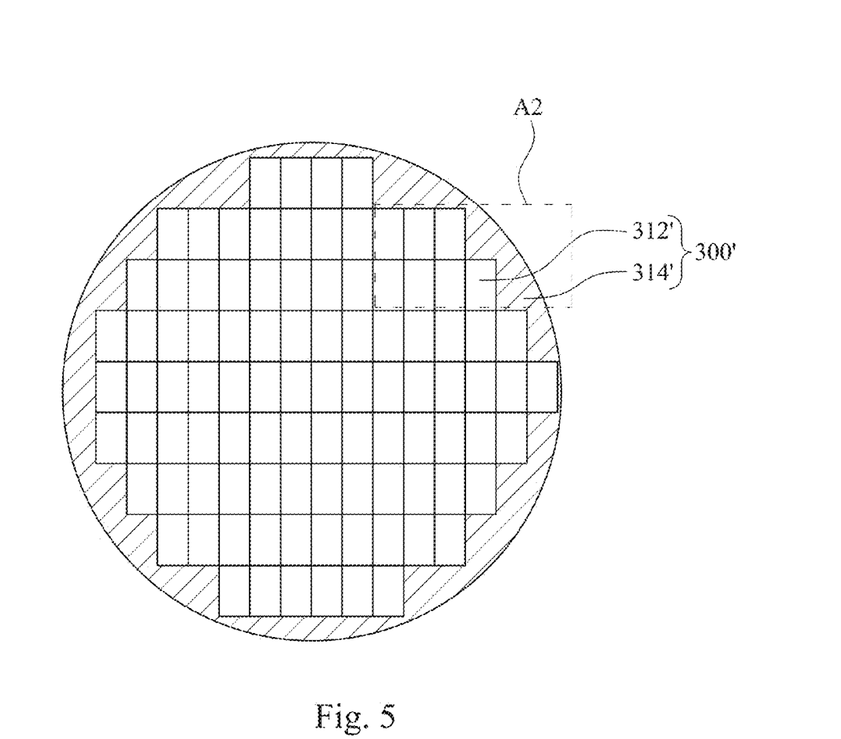
FIG. 5 is a top view of another semiconductor element when being inspected by a photosensitive element shown in FIG. 1.
Figure 6:
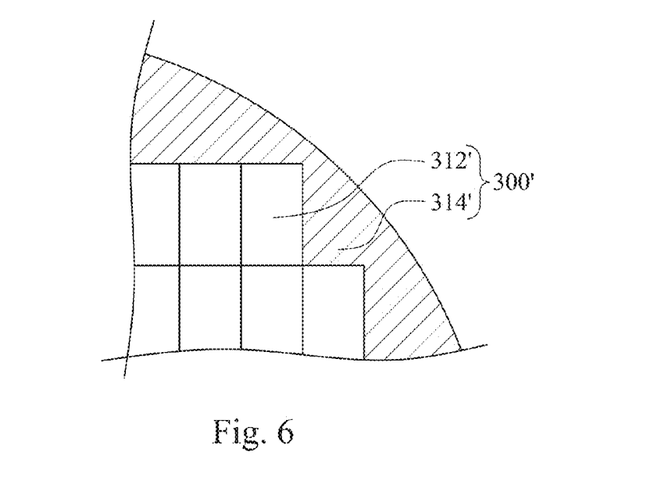
FIG. 6 is a partial enlarged view of the semiconductor element within an inspection area of the photosensitive element shown in FIG. 5.

FIG. 5 is a top view of another semiconductor element 300' when being inspected by the photosensitive element 120 shown in FIG. 1. FIG. 6 is a partial enlarged view of the semiconductor element 300' within an inspection area A2 of the photosensitive element 120 shown in FIG. 5. As shown in FIG. 5 and FIG. 6, the semiconductor element 300' has a plurality of complete dies 312' and partial dies 314'. The partial dies 314' surrounds the complete dies 312'. That is to say, the partial dies 314' are at the edge portion of the semiconductor element 300'.

The photosensitive element 120 (see FIG. 1) may position the inspection area A2 on a portion of the complete dies 312' and a portion of the partial dies 314'. The difference between this embodiment and the embodiment shown in FIG. 3 and FIG. 4 is that the complete dies 312' are slender dies.

As shown in FIG. 2 and FIG. 5, the controller 130 can drive the photosensitive element 120 to inspect the defects of the complete dies 312' and the defects of the partial dies 314'. In operation, the first driving module 132 electrically connected to the photosensitive element 120 drives the photosensitive element 120 to inspect the defects of the complete dies 312', and the second driving module 134 electrically connected to the photosensitive element 120 drives the photosensitive element 120 to inspect the defects of the partial dies 314'.

When the photosensitive element 120 inspects the semiconductor element 300', the photosensitive element 120 may position an inspection area A2 on a portion of the complete dies 312' and a portion of the partial dies 314'. Users can choose a function on the inspection setting device 140 to inspect the defects of the complete dies 312', the defects of the partial dies 314', or the combinations thereof, such that an inspection signal may be sent to the photosensitive element 120.

As shown in FIG. 1 and FIG. 5, the inspection area A2 may be smaller than the semiconductor element 300', but the present disclosure is not limited in this regard. However, the inspection area A2 on the semiconductor element 300' can move along with the photosensitive element 120, such that the defects of the complete dies 312' and the defects of the partial dies 314' can be scanned by the inspection area A2 of the photosensitive element 300.

Figure 7:
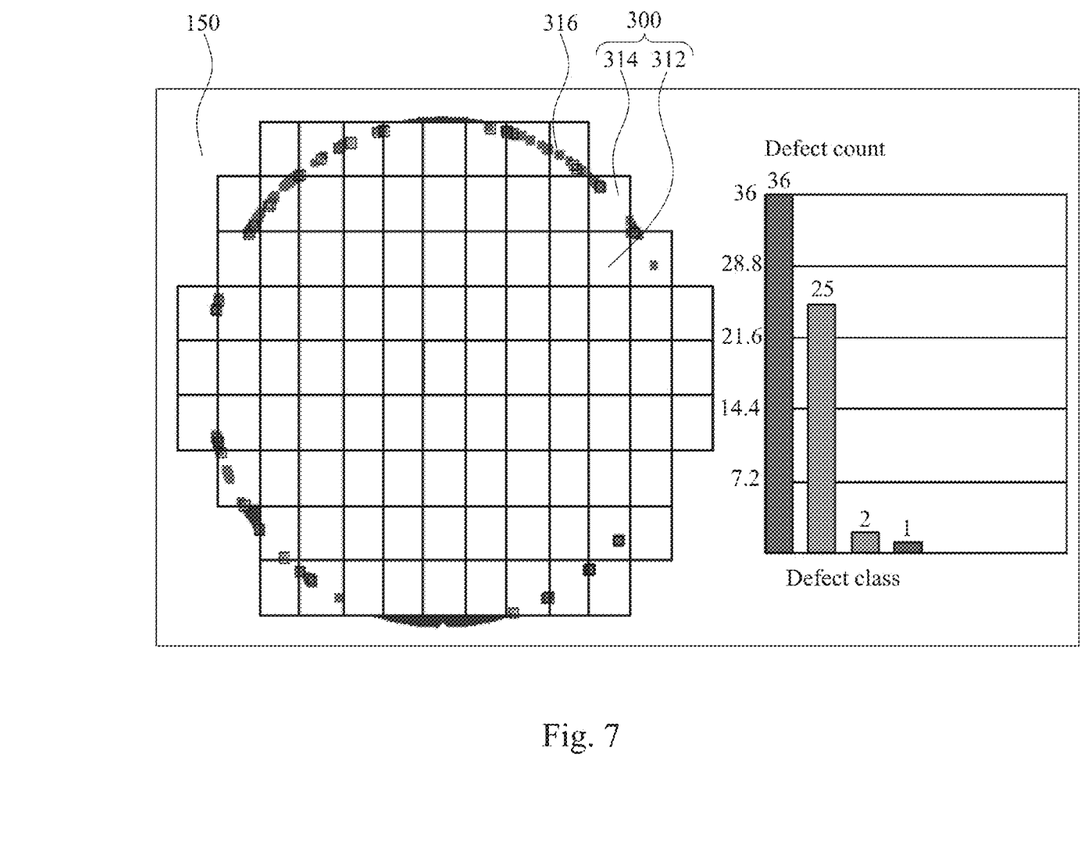
FIG. 7 is a schematic view of a data analysis device when displaying a defect information shown in FIG. 2.

FIG. 7 is a schematic view of a data analysis device 150 when displaying a defect information shown in FIG. 2. As shown in FIG. 2 and FIG. 7, the defect inspection apparatus 100 further includes the data analysis device 150 and a feedforward device 160. The data analysis device 150 is electrically connected to the photosensitive element 120, and the feedforward device 160 is electrically connected to the data analysis device 150 and a previous process tool 210. Before the defect inspection apparatus 100 inspects the semiconductor element 300 (see FIG. 1), the previous process tool 210 applies a treatment to the semiconductor element 300. For example, the previous process tool 210 may be a CVD (chemical vapor deposition) equipment, a PVD (physical vapor deposition) equipment, or a CMP (chemical mechanical planarization) equipment.

After the photosensitive element 120 inspects the semiconductor element 300, a defect information of the complete dies 312 and the partial dies 314 is received from the photosensitive element 120. Thereafter, the data analysis device 150 analyzes the distribution of the defects 316 of the complete dies 312 and the partial dies 314 and displays a defect distribution graph of the defect information on the monitor thereof.

Furthermore, the data analysis device 150 can determine whether the defect information is in-spec or out-spec defined by users. When the defect information is in-spec, the data analysis device 150 may send a release signal to the controller 130 to release the semiconductor element 300 to a next process step. The defect information is in-spec means that the previous process tool 210 is under a normal operation. The data analysis device 150 may send a running signal to the previous process tool 210, such that the previous process tool 210 keeps running. As a result, the previous process tool 210 can keep applying a treatment to other semiconductor elements 300.

On the other hand, the defect information is out-spec means that the previous process tool 210 is under an error operation, such as the occurrence of hardware problems or process parameter problems of the previous process tool 210. In some embodiments, the data analysis device 150 may send a stop signal to the previous process tool 210, such that the previous process tool 210 stops running. As a result, the previous process tool 210 can stop applying a treatment to other semiconductor elements 300. At this moment, users can check the hardware or process parameter problems of the previous process tool 210.

In some embodiments, the data analysis device 150 does not send the stop signal to the previous process tool 210, but sends a compensation value to the previous process tool 210. The compensation value is formed in accordance with the defect information. As a result, the previous process tool 210 can tune process parameters in accordance with the compensation value that is sent from the data analysis device 150. For example, the process parameters may include exposure energy, etching rate, polish time, and EBR (edge bead removal) range. After the process parameters are modified, the previous process tool 210 can recover to run product.

Referring back to FIG. 2 and FIG. 3, the defect inspection apparatus 100 can inspect the complete and partial dies 312, 314 of the semiconductor element 300. Therefore, additional devices (e.g., OM or SEM) are not required to use to check the defects of the partial dies 314. When the processes for manufacturing the semiconductor element 300 have vibrations, the defect inspection apparatus 100 can inspect the defects of the complete dies 312 and the partial dies 314 at the same time. As a result, the time for confirming the partial die area through additional devices may be reduced.

Figure 8:
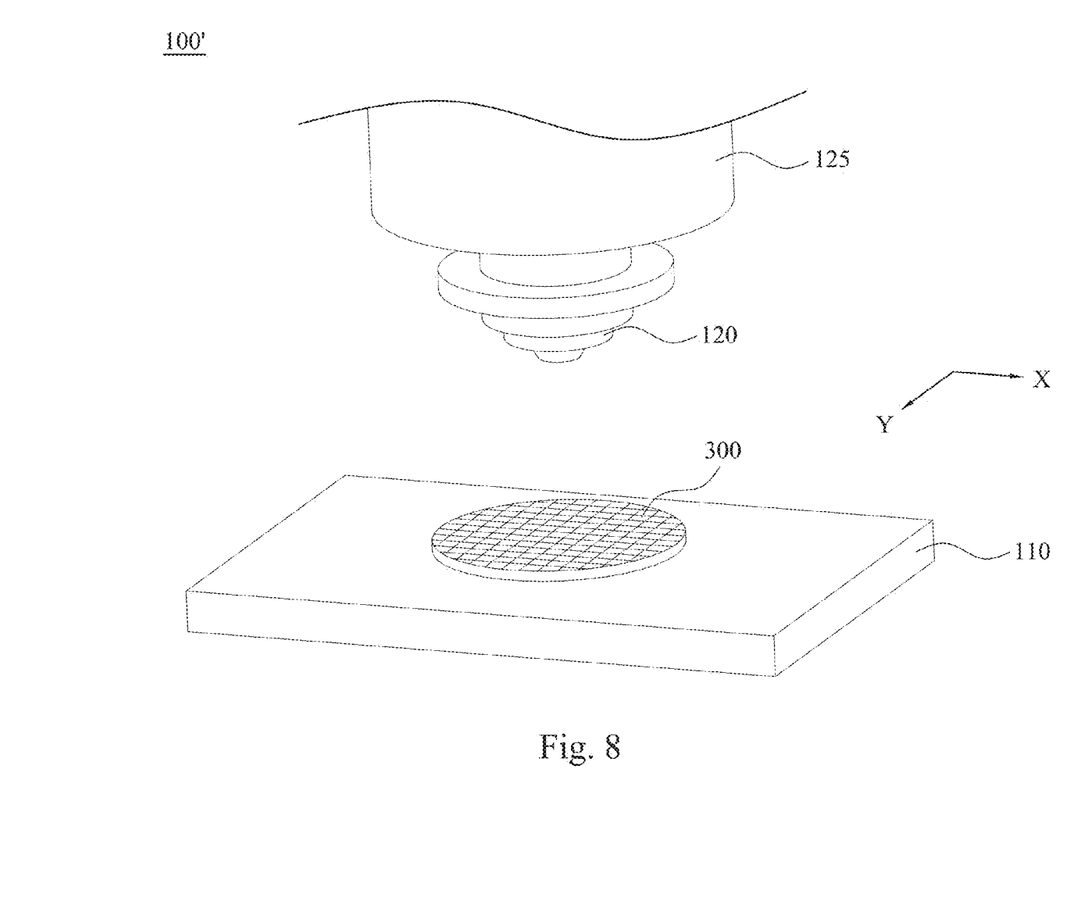
FIG. 8 is a perspective view of a defect inspection apparatus in accordance with some embodiments of the present disclosure.
Figure 9:
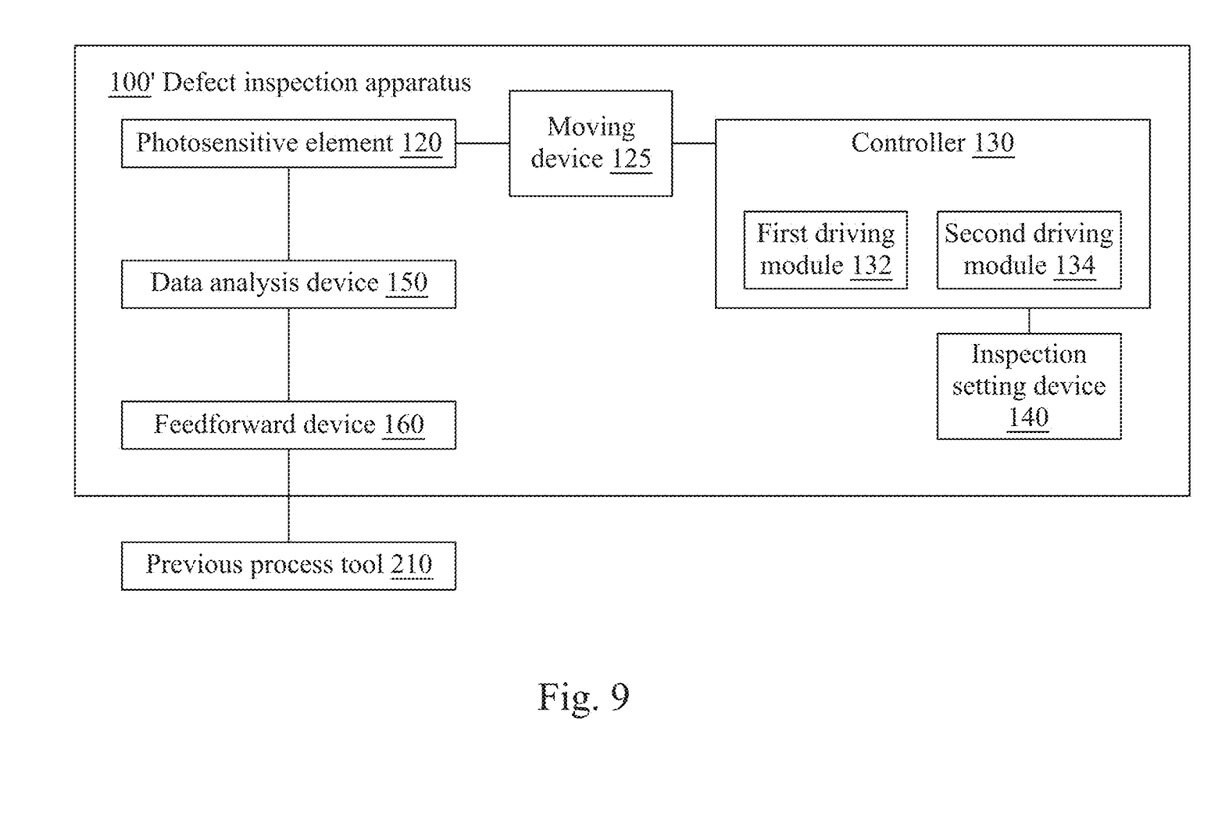
FIG. 9 is a block diagram of the defect inspection apparatus connected to the previous process tool shown in FIG. 8.

FIG. 8 is a perspective view of a defect inspection apparatus 100' in accordance with some embodiments of the present disclosure. FIG. 9 is a block diagram of the defect inspection apparatus 100' connected to the previous process tool 210 shown in FIG. 8. As shown in FIG. 8 and FIG. 9, the defect inspection apparatus 100' includes the stage 110, the photosensitive element 120, the moving device 125, the controller 130, the inspection setting device 140, the data analysis device 150, and the feedforward device 160.

The difference between this embodiment and the embodiment shown in FIG. 2 is that the moving device 125 is electrically connected between the photosensitive element 120 and the controller 130, such that the controller 130 can obtain the position information of the photosensitive element 120 through the moving device 125.

The stage 110 can support the semiconductor element 300, such as a wafer. The photosensitive element 120 is located above the stage 110, and may include a charge coupled device (CCD) camera. The controller 130 is electrically connected to the photosensitive element 120. In operation, the controller 130 drives the photosensitive element 120 to inspect the defects of the semiconductor element 300.

As shown in FIG. 3 and FIG. 9, the controller 130 can drive the photosensitive element 120 to inspect the defects of the complete dies 312 and the defects of the partial dies 314. The controller 130 includes the first driving module 132 and the second driving module 134. The first and second driving modules 132, 134 are electrically connected to the photosensitive element 120 through the moving device 125. In operation, the first driving module 132 drives the photosensitive element 120 to inspect the defects of the complete dies 312, and the second driving module 134 drives the photosensitive element 120 to inspect the defects of the partial dies 314.

When the photosensitive element 120 inspects the semiconductor element 300, the photosensitive element 120 may position an inspection area A1 on a portion of the complete dies 312 and a portion of the partial dies 314. The inspection area A1 on the semiconductor element 300 can move along with the photosensitive element 120, such that the defects of the complete dies 312 and the defects of the partial dies 314 can be scanned by the inspection area A1 of the photosensitive element 300.

The inspection setting device 140 is electrically connected to the first and second driving modules 132, 134 of the controller 130. Users can choose a function on the inspection setting device 140 to inspect the defects of the complete dies 312, the defects of the partial dies 314, or the combinations thereof, such that an inspection signal may be sent to the photosensitive element 120.

Figure 10:
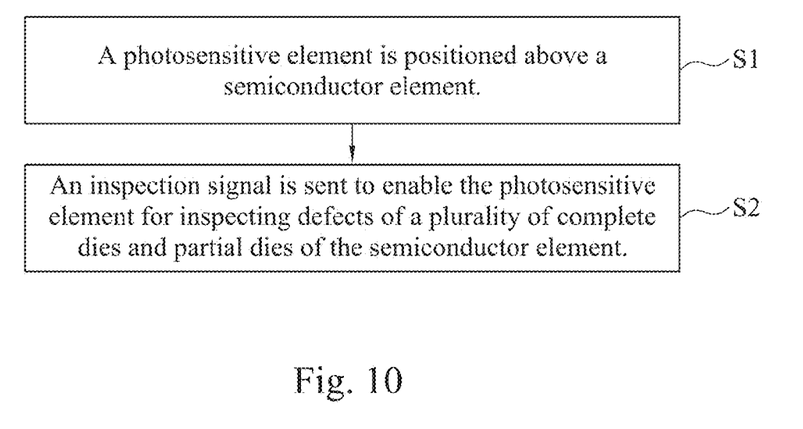
FIG. 10 is a flow chart of a defect inspection method in accordance with some embodiments of the present disclosure.

FIG. 10 is a flow chart of a defect inspection method in accordance with some embodiments of the present disclosure. As shown in FIG. 10, the defect inspection method includes the operations below. In step S1, a photosensitive element is positioned above a semiconductor element.

Thereafter in step S2, an inspection signal is sent to enable the photosensitive element for inspecting defects of a plurality of complete dies and partial dies of the semiconductor element. The inspection signal may be sent by an inspection setting device. Users can set a recipe in the inspection setting device for driving the photosensitive element to inspect the defects of the complete dies and the partial dies of the semiconductor element.

As a result, users can not only understand the defect contribution of the complete dies, but also understand the defect contribution of the partial dies, such that the state of previous process tools forming the defects of the complete and partial dies can be know by users.

Figure 11:
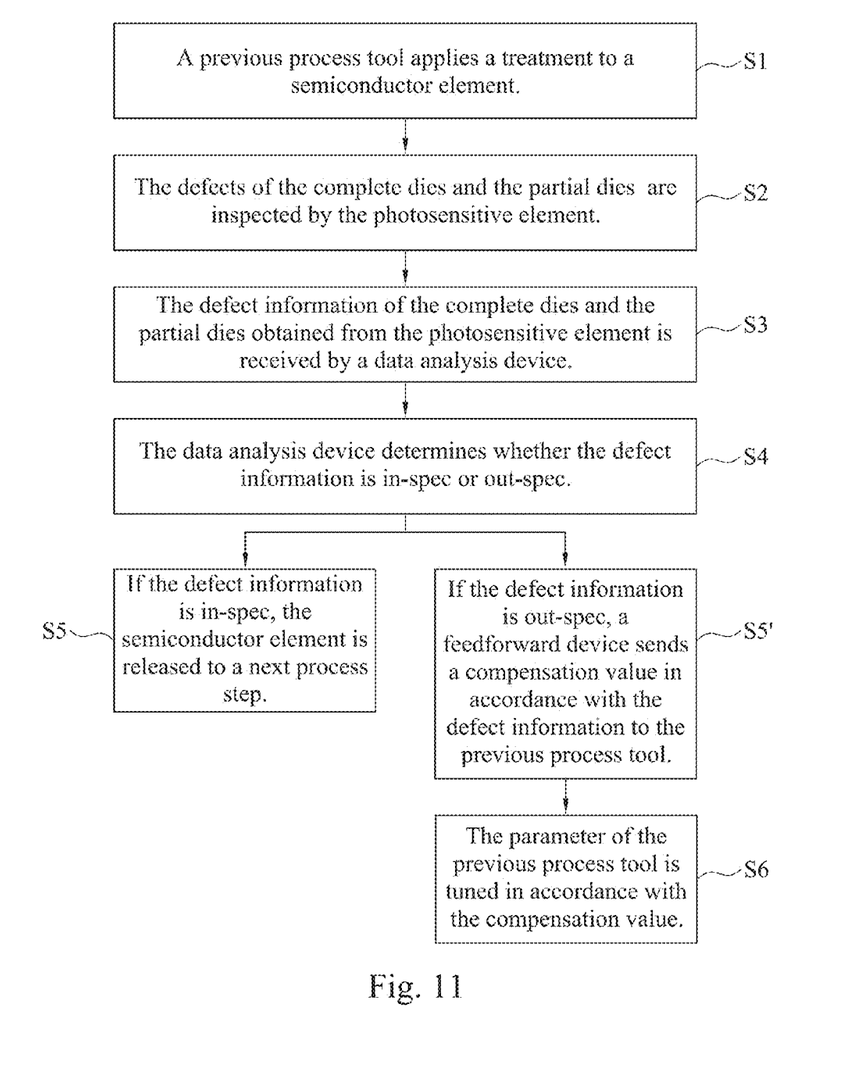
FIG. 11 is a flow chart of a defect inspection method in accordance with some embodiments of the present disclosure.

FIG. 11 is a flow chart of a defect inspection method in accordance with some embodiments of the present disclosure. As shown in FIG. 11, the defect inspection method includes the operations below. In step S1, a previous process tool applies a treatment to a semiconductor element. Next in step S2, the defects of the complete dies and the partial dies are inspected by the photosensitive element. Thereafter in step S3, the defect information of the complete dies and the partial dies obtained from the photosensitive element is received by a data analysis device. Next in step S4, the data analysis device determines whether the defect information is in-spec or out-spec.

Thereafter in step S5 or S5', if the defect information is in-spec, the semiconductor element is released to a next process step. If the defect information is out-spec, a feedforward device sends a compensation value in accordance with the defect information to the previous process tool.

Finally in step S6, the parameter of the previous process tool is tuned in accordance with the compensation value.

Compared with conventional scan tools, the defect inspection apparatus and method of the present disclosure can inspect the complete and partial dies of the semiconductor element. Therefore, additional devices (e.g., OM or SEM) are not required to use to check the defects of the partial dies. When the processes of the semiconductor element have vibrations, the defect inspection apparatus and method can inspect the defects of the complete dies and the partial dies at the same time. As a result, the time for confirming the partial die area through additional devices may be reduced.

In this document, the term "contact" is also used to indicate the term "via."

In this document, the term "coupled" may also be termed as "electrically coupled", and the term "connected" may be termed as "electrically connected". "Coupled" and "connected" may also be used to indicate that two or more elements cooperate or interact with each other.

The above illustrations include exemplary operations, but the operations are not necessarily performed in the order shown. Operations may be added, replaced, changed order, and/or eliminated as appropriate, in accordance with the spirit and scope of various embodiments of the present disclosure.

In some embodiments, a defect inspection apparatus is disclosed that includes a stage, a photosensitive element, and a controller. The stage can support a semiconductor element that has a plurality of complete dies and partial dies surrounding the complete dies. The photosensitive element is disposed above the stage. The controller is electrically connected to the photosensitive element to drive the photosensitive element to inspect the defects of the complete dies and the partial dies.

Also disclosed is a defect inspection apparatus that includes a stage and a photosensitive element. The stage can support a semiconductor element that has a plurality of complete dies and partial dies surrounding the complete dies. The photosensitive element is disposed above the stage and has an inspection area. When the semiconductor element is on the stage, the inspection area is positioned on a portion of the complete dies and a portion of the partial dies.

A defect inspection method is also disclosed that includes the operations below. A semiconductor element and a photosensitive element disposed above the semiconductor element is provided. An inspection signal is sent to the photosensitive element. Defects of a plurality of complete dies and partial dies of the semiconductor element are inspected by the photosensitive element.

As is understood by one of ordinary skill in the art, the foregoing embodiments of the present disclosure are illustrative of the present disclosure rather than limiting of the present disclosure. It is intended to cover various modifications and similar arrangements included within the spirit and scope of the appended claims, the scope of which should be accorded with the broadest interpretation so as to encompass all such modifications and similar structures.

What is claimed is:

1. A defect inspection apparatus comprising:
    a stage for supporting a semiconductor element that has a plurality of complete dies and partial dies surrounding the complete dies;
    a photosensitive element disposed above the stage; and
    a controller electrically connected to the photosensitive element for driving the photosensitive element to inspect defects of the complete dies and the partial dies.

2. The defect inspection apparatus of claim 1, wherein the controller comprises:
    a first driving module electrically connected to the photosensitive element for driving the photosensitive element to inspect the defects of the complete dies; and
    a second driving module electrically connected to the photosensitive element for driving the photosensitive element to inspect the defects of the partial dies.

3. The defect inspection apparatus of claim 2, further comprising:
    an inspection setting device electrically connected to the first and second driving modules.

4. The defect inspection apparatus of claim 1, further comprising:
    a data analysis device electrically connected to the photosensitive element.

5. The defect inspection apparatus of claim 4, further comprising:
    a feedforward device electrically connected to the data analysis device and a previous process tool.

6. The defect inspection apparatus of claim 1, wherein the photosensitive element comprises a charge coupled device (CCD) camera.

7. A defect inspection apparatus comprising:
    a stage for supporting a semiconductor element that has a plurality of complete dies and partial dies surrounding the complete dies; and
    a photosensitive element disposed above the stage and configured to inspect defects of the complete dies and the partial dies, the photosensitive element having an inspection area, wherein when the semiconductor element is on the stage, the inspection area is positioned on a portion of the complete dies and a portion of the partial dies.

8. The defect inspection apparatus of claim 7, further comprising:
    a moving device connected to the photosensitive element for moving the photosensitive element above the semiconductor element, such that the defects of the complete dies and the partial dies are scanned by the inspection area of the photosensitive element.

9. The defect inspection method of claim 7, wherein the inspection area is smaller than the semiconductor element.

10. A defect inspection method comprising:
    positioning a photosensitive element above a semiconductor element; and
    sending an inspection signal to enable the photosensitive element for inspecting defects of a plurality of complete dies and partial dies of the semiconductor element.

11. The defect inspection method of claim 10, further comprising:
    receiving a defect information of the complete dies and the partial dies from the photosensitive element.

12. The defect inspection method of claim 11, further comprising:
    determining whether the defect information is in-spec or out-spec.

13. The defect inspection method of claim 12, wherein when the defect information is in-spec, the defect inspection method further comprises:
    releasing the semiconductor element to a next process step.

14. The defect inspection method of claim 13, further comprising:
    sending a running signal to a previous process tool that applies a treatment to the semiconductor element before inspecting the defects, such that the previous process tool keeps applying a treatment to another semiconductor element.

15. The defect inspection method of claim 11, wherein when the defect information is out-spec, the defect inspection method further comprises:
    sending a stop signal to a previous process tool that applies a treatment to the semiconductor element before inspecting the defects, such that the previous process tool stops applying a treatment to another semiconductor element.

16. The defect inspection method of claim 11, wherein when the defect information is out-spec, the defect inspection method further comprises:
    sending a compensation value in accordance with the defect information to a previous process tool that applies a treatment to the semiconductor element before inspecting the defects.

17. The defect inspection method of claim 16, further comprising:
    tuning a parameter of the previous process tool in accordance with the compensation value.

18. The defect inspection method of claim 11, further comprising:
    displaying a defect distribution graph of the defect information on a monitor.

19. The defect inspection method of claim 10, wherein inspecting the defects of the complete dies and the partial dies further comprises:
    positioning an inspection area of the photosensitive element on a portion of the complete dies and a portion of the partial dies.

20. The defect inspection method of claim 19, further comprising:
    moving the photosensitive element above the semiconductor element, such that the defects of the complete dies and the partial dies are scanned by the inspection area of the photosensitive element.

* * * * *